United States Patent [19]

Ohlendorf et al.

[11] 4,279,904
[45] Jul. 21, 1981

[54] 3-AMINO-1-BENZOXEPINE DERIVATIVES AND THEIR SALTS AND PHARMACEUTICAL COMPOSITIONS THEREOF

[75] Inventors: Heinrich-Wilhelm Ohlendorf, Hanover; Klaus-Ullrich Wolf, Haenigsen; Wilhelm Kaupmann, Hannover-Kirchrode; Henning Heinemann, Hanover, all of Fed. Rep. of Germany

[73] Assignee: Kali-Chemie Pharma GmbH, Hanover, Fed. Rep. of Germany

[21] Appl. No.: 173,075

[22] Filed: Jul. 28, 1980

[30] Foreign Application Priority Data

Aug. 2, 1979 [DE] Fed. Rep. of Germany ....... 2931399

[51] Int. Cl.$^3$ ................... A61K 31/335; C07D 313/08
[52] U.S. Cl. ................... 424/246; 260/326.5 CA; 548/215; 548/240; 260/326.5 S; 548/300; 548/356; 260/330; 260/333; 260/340.3; 260/340.5 R; 424/248.52; 424/248.56; 424/250; 424/251; 424/267; 424/270; 424/272; 424/273 R; 424/274; 424/275; 424/278; 424/282; 544/3; 544/54; 544/55; 544/58.7; 544/60; 544/63; 544/96; 544/147; 544/238; 544/333; 544/376; 546/196; 548/146; 548/214
[58] Field of Search ............... 260/326.5 S, 326.5 CA, 260/330, 333, 340.3, 340.5 R; 424/246, 248.52, 248.56, 250, 251, 267, 270, 272, 273 R, 274, 275, 278, 282; 544/3, 54, 55, 58.7, 60, 63, 96, 147, 238, 333, 376; 546/196; 548/146, 214, 215, 240, 300, 356

[56] References Cited
U.S. PATENT DOCUMENTS 3,991,082 11/1976 Klutchko et al. ............... 260/333 X
4,153,612 5/1979 McCall ............... 260/333 X

OTHER PUBLICATIONS

Huckle et al., J. Chem. Soc.(c), 1971, pp. 2252-2260.
Tandon et al., Indian Journal of Chemistry, vol. 13, (1975), pp. 1-8.
Tandon et al., Indian Journal of Chemistry, vol. 15B, (1977), pp. 264-266.
Khanna et al., J. Indian Chem. Soc., vol. 51(1), (1974), pp. 289-303.

Primary Examiner—Richard Raymond

Attorney, Agent, or Firm—Schwartz, Jeffery, Schwaab, Mack, Blumenthal & Koch

[57] ABSTRACT

Novel 3-amino-1-benzoxepine derivatives and methods for their production are disclosed. These derivatives correspond to the Formula I

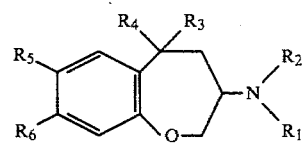

wherein:
R$_1$ and R$_2$ independently of one another are hydrogen,
C$_1$-C$_5$ alkyl,
C$_1$-C$_5$ alkyl substituted with a terminal phenyl, or a phenyl containing one or two halogens, methyl or methoxy groups, a 3,4-methylenedioxy or a 3,4-ethylenedioxy group,
C$_2$-C$_5$ alkyl substituted with terminal hydroxy or methoxy or,
C$_3$-C$_4$ alkenyl; or
one of R$_1$ and R$_2$ are hydrogen or a C$_1$-C$_5$ alkyl and the other is a C$_2$-C$_5$ alkyl substituted with a terminal NR$_7$R$_8$;
R$_7$ and R$_8$ independently of one another are hydrogen or C$_1$-C$_5$ alkyl; or
R$_7$ and R$_8$ are together a 5 to 7 member ring or said ring having heterogeneous oxygen, sulfur or nitrogen, or
R$_1$ and R$_2$ are together a 5 to 7 member ring or said ring having heterogeneous oxygen, sulfur or NR$_9$;
R$_9$ is hydrogen, methyl, benzyl, or phenyl;
one of R$_3$ and R$_4$ is hydrogen and the other hydroxy, or
R$_3$ and R$_4$ together are oxygen;
R$_5$ and R$_6$ independently of one another are hydrogen, halogen, C$_1$-C$_4$ alkyl, C$_1$-C$_4$ alkoxy or C$_1$-C$_4$ alkylthio; or
one of R$_5$ and R$_6$ is trifluoromethyl or nitro and the other is hydrogen; the stereo isomers and the acid addition salts thereof. These compounds have a favorable effect upon the motility of the gastrointestinal tract and, therefore, constitute the active ingredient of pharmaceutical compositions and methods for the treatment of motility disorders.

9 Claims, No Drawings

3-AMINO-1-BENZOXEPINE DERIVATIVES AND THEIR SALTS AND PHARMACEUTICAL COMPOSITIONS THEREOF

BACKGROUND OF THE INVENTION

1. Field of the Invention

The present invention relates to novel and useful 3-amino-1-benzoxepine derivatives and the salts of such derivatives, methods of their production as well as substances containing pharmaceutically effective amounts of such derivatives. More particularly, the present invention relates to certain pharmaceutically active 3-amino-1-benzoxepine derivatives, their acid addition salts as well as to the process of producing these pharmaceutically active derivatives and acid addition salts and the pharmaceutical compositions themselves as well as to a method of using such compositions in therapy and more particularly, for the treatment of certain gastrointestinal disorders and diseases.

2. Background of the Prior Art

It is known that a considerable number of gastroenterological complaints are caused by functional disturbances. Disorders of the motility, more particularly of the stomach and its sphincters, have been recognized more and more as the cause of various diseases and disorders of the gastro-intestinal tract. See, for instance, "Leber, Magen, Darm" (liver, stomach intestines) Vol. 8 (1978) No. 4, pages 177 to 182 and pages 184 to 190 or, respectively, "Internist" Vol. 20, 1979, pages 10 to 17. More particularly, a pylorus incompetence which is made responsible for the duodeno-gastric reflux, is discussed extensively in connection with a search for the pathologic-physiological causes of various disturbances and disorders of the gastro-intestinal tract. See, for instance, "Digestive Diseases" Vol. 21, 1976 No. 2, pages 165 to 173. According to these discussions and publications, the reflux gastritis, the ulcus ventriculi and duodeni, as well as the sense of fullness, nausea, and epigastric pain without anatomically recognizable reasons are caused, or are complicated in their course by disorders of the gastric passage.

Heretofore no satisfactory pharmaceutical agent for treating disorders of the gastro-intestinal motility was known.

SUMMARY OF THE INVENTION

It is one object of the present invention to provide novel and useful 3-amino-1-benzoxepine compounds and their acid addition salts.

Another object of the invention is to provide simple and advantageous processes of producing such novel 3-amino-1-benzoxepine compounds and their acid addition salts.

Still another object of the present invention is to provide compositions containing such 3-amino-1-benzoxepine compounds and their acid addition salts and, especially, pharmaceutical compositions containing same.

A further object of the present invention is to provide a novel and highly effective method of treating certain gastro-intestinal disorders and diseases by administering such pharmaceutical compositions to patients.

Other objects and advantageous features of the present invention will become apparent as the description proceeds.

In principle, the aim of the present invention is to provide the medical profession with novel 3-amino-1-benzoxepine compounds having valuable pharmacological and therapeutic properties.

Surprisingly, it was found that the novel compounds have a favorable effect upon gastric motility.

Thus, the present invention comprises novel 3-amino-1-benzoxepine compounds of the following Formula I:

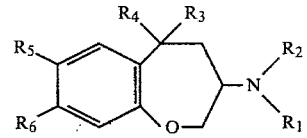

wherein:
$R_1$ and $R_2$ independently of one another are
  hydrogen,
  $C_1$–$C_5$ alkyl,
  $C_1$–$C_5$ alkyl substituted with a terminal phenyl, or a phenyl containing one or two halogens, one or two methyl or methoxy groups, 3,4-methylene dioxy or 3,4-ethylenedioxy group,
  $C_2$–$C_5$ alkyl substituted with terminal hydroxy or methoxy or,
  $C_3$–$C_4$ alkenyl; or
one of $R_1$ and $R_2$ are hydrogen or a $C_1$–$C_5$ alkyl and the other is a $C_2$–$C_5$ alkyl substituted with a terminal $NR_7R_8$;
$R_7$ and $R_8$ independently of one another are hydrogen or $C_1$–$C_5$ alkyl; or
$R_7$ and $R_8$ are together a 5 to 7 member ring or said ring having heterogeneous oxygen, sulfur or nitrogen, or
$R_1$ and $R_2$ are together a 5 to 7 member ring or said ring having heterogeneous oxygen, sulfur or $NR_9$;
$R_9$ is hydrogen, methyl, benzyl or phenyl;
one of $R_3$ and $R_4$ is hydrogen and the other hydroxy; or
$R_3$ and $R_4$ together are oxygen;
$R_5$ and $R_6$ independently of one another are hydrogen, halogen, $C_1$–$C_4$ alkyl, $C_1$–$C_4$ alkoxy or $C_1$–$C_4$ alkylthio; or
one of $R_5$ and $R_6$ is trifluoromethyl or nitro and the other is hydrogen.

The present invention also includes the stereo isomers and the acid addition salts of the compound of Formula I.

The 3-amino-1-benzoxepine derivatives of Formula I wherein one of the $R_3$ and $R_4$ groups are hydrogen and the other is hydroxy results in the formation of racemates with the respective cis- and trans-configuration of the carbinol and the amine group.

The compounds of Formula I contain at least one asymetric carbon atom and therefore exist in the D and L form. The invention encompasses all of the racemic mixtures of pure D and L forms of the compounds.

Suitable lower alkyl groups and groups comprising the $R_1$ and $R_2$ moieties include both straight chain and branched chain lower alkyl groups of one to five carbon atoms. For example, methyl, ethyl, propyl, isopropyl, butyl, isobutyl, tert.-butyl, pentyl, isopentyl, neopentyl, allyl, 2-butenyl, 3-butenyl and the like. Preferred are the compounds in which only one of the $R_1$ and $R_2$ groups is a substituted alkyl and the other is a hydrogen or $C_1$–$C_5$ alkyl.

The above-mentioned specific alkyl groups containing one to five carbon atoms are also applicable for $R_7$ and $R_8$.

As examples of substitutions wherein alkyl groups are joined through a nitrogen atom, either directly or through a hetero atom are the following: pyrrolidine, piperidine, azacycloheptane, morpholine, thiomorpholine, piperazine and homo-piperazine wherein it is possible to substitute the nitrogen with methyl, benzyl or phenyl. Preferred are the alkyl groups joined in the form of five and six membered rings.

Substituents $R_5$ and $R_6$ on the phenyl ring may comprise the halogen atoms fluorine, chlorine, bromine and iodine. Especially preferred are fluorine, chlorine, and bromine. The $C_1$–$C_4$ alkyl portion of the alkyl, alkoxy or alkylthio groups can be straight chain or branched wherein the methyl groups are especially preferred with multi substitutions on the phenyl ring. Thus, methyl, methoxy, methylthio or methylenedioxy are preferred. If one of the substituents is nitro or trifluoromethyl mono-substitution is preferred.

The 3-amino-1-benzoxepine compounds of Formula I can, when desired, be converted to their physiologically compatible acid addition salts by treatment with an inorganic or organic acid in the conventional manner. As suitable acids for producing the acid addition salts hydrochloric acid, hydrobromic acid, sulfuric acid, nitric acid, o-phosphoric acid, maleic acid, cyclohexyl-amino sulfonic acid, amido sulfonic acid or p-toluene sulfonic acid, are preferred.

The invention also concerns the method of producing the 3-amino-1-benzoxepine derivatives of Formula I

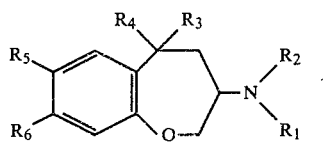

wherein $R_1$, $R_2$, $R_3$, $R_4$, $R_5$ and $R_6$ are defined as above, their stereo isomers as well as the acid addition salts. The method comprises reducing the 3-amino-1-benzoxepin-5(2H)-one derivatives of the Formula II

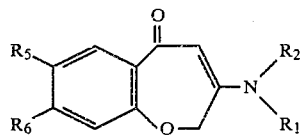

wherein $R_1$, $R_2$, $R_5$ and $R_6$ are defined as above in an inert solvent in a temperature range between −70° C. and the reflux temperature of the solvent and, if desired conducting the reduction in the presence of an inorganic or organic acid with a hydride-reduction agent or subjecting the compound in an inert solvent to catalytic hydrogenation with hydrogen, (a) if desired, the 3,4 double bond is hydrogenated and the 5-keto group is reduced to a 5-hydroxy group and the 2,3,4,5-tetrahydro-3-amino-1-benzoxepin-5-ol derivative of Formula I is isolated, (b) if desired, the 3,4 double bond is hydrogenated and the 3-amino-3,4-dihydro-1-benzoxepin-5(2H)-one derivative of Formula I is isolated, (c) if desired, the 3-amino-3,4-dihydro-1-benzoxepin-5(2H)-one derivative of Formula I is reduced to the 2,3,4,5-tetrahydro-3-amino-1-benzoxepin-5-ol derivative of Formula I and isolated, (d) if desired, the free base formed in the foregoing (a), (b) and (c) is converted to the corresponding acid addition salt or the acid addition salt transformed into the free base, (e) if desired, the compounds of Formula I obtained under the foregoing (a) or (c) are separated into the racemic-cis- and racemic-trans-2,3,4,5-tetrahydro-3-amino-1-benzoxepin-5-ol derivatives of Formula I and, if applicable, isolated in the form of their acid addition salts, (f) if desired, the racemic mixture of compounds of Formula I are split into their optical opposites, (g) if desired, the N-alkyl compounds are produced by subsequent alkylation.

In all instances the desired compound is recovered in suitable form after the final treatment.

The starting materials necessary to produce the 3-amino-1-benzoxepine derivatives of the present invention, as well as the method of preparing the starting materials are disclosed in our copending application Ser. No. 173,076 filed July 28, 1980, which disclosure is hereby incorporated by reference. The starting materials themselves represent pharmacologically valuable compounds which above all produce a retarding and regulating effect on the spasm of the smooth, muscularature of the stomach-intestinal canal.

The compositions can, for example, be obtained by reacting in an inert solvent a 2,3,4,5-tetrahydro-1-benzoxepin-3,5-di-one derivative of Formula III

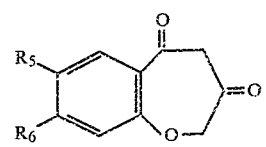

wherein $R_5$ and $R_6$ are defined as above,
(a) with an amine of the Formula IV

wherein $R_1$ and $R_2$ are defined as above, or
(b) reacting the 2,3,4,5-tetrahydro-1-benzoxepin-3,5-di-one derivative of Formula III with an acid halide in an inert solvent to form the compound of Formula V

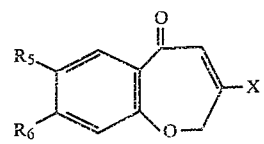

wherein $R_5$ and $R_6$ are defined as above and X is chlorine or bromine, converting these through transformation with an amine of the Formula IV into the compounds of Formula II, isolating the free base and, as desired, converting to the acid addition salts or isolating from the acid addition salts the free base.

In another embodiment of the present invention, the 3,4-double bond is hydrogenated and the 5-keto group is reduced to a 5-hydroxy group in a single step by reducing the compounds of Formula II either in a neutral or weakly acid range, in particular in a pH range of 4 to 7 with sodium borohydride, or in the acid range, preferably between pH 3 to 4 with sodium cyanoborohydride.

As suitable solvents, for example, dioxane, tetrahydrofuran, dimethylformamide, ethyleneglycol dimethylether or diethyleneglycol dimethylether may be used. Low molecular alcohols such as methanol, ethanol or isopropanol, may also be used. Inorganic or organic acids, such as for example acetic acid, p-toluenesulfonic acid, benzenesulfonic acid, hydrochloric acid or sulfuric acid may be utilized to adjust the pH range in a favorable manner.

Simultaneous hydrogenation and reduction is also possible by reducing the compounds of Formula II with hydrogen in the presence of Raney nickel in a protic solvent, preferably ethanol or isopropanol, in a conventional manner.

Thereby, the rac.-2,3,4,5-tetrahydro-3-amino-1-benzoxepin-5-ol compounds of Formula I are obtained. These compounds may be isolated from the reaction mixture in the form of their free bases or their acid addition salts.

To separate the racemates with cis- and trans-configurations of the carbinol and amine groups, it is possible in a conventional manner to expose these free bases or their acid addition salts to fractionating crystallization in suitable solvents, such as, for example, lower alcohols. Particularly suitable acids for the formation of salts are, among others, maleic acid, p-toluenesulfonic acid and cyclohexylaminosulfonic acid. Separation of the racemates may also be accomplished by means of chromatography of the free bases with suitable solvents on silica gel or aluminum oxide.

The rac.-cis and rac.-trans-2,3,4,5-tetrahydro-3-amino-1-benzoxepin-5-ols of Formula I may be separated in a conventional manner by means of reaction with suitable, optically active acids, such as for example tartaric acid, o,o'-dibenzoyltartaric acid, mandelic acid, di-0-isopropylidene-2-oxo-L-gulonic acid and subsequent fractionating crystallization of the salts obtained in their optically active isomers. The free bases may be released from these salts and the bases, if so desired, and converted to their pharmacologically compatible salts. The racemic compounds and their isomers, together with their acid addition salts, may be purified by means of recrystallization from solvents, such as lower alcohols and/or ether.

The hydrogenation of the 3,4 double bond in the compounds of Formula II in keeping with step (b) is possible in the weakly acidic range, preferably at pH 4 to 6, by means of sodium cyanoborohydride in solvents such as for example lower alcohols, dioxane, tetrahydrofuran, dimethylformamide, ethyleneglycol dimethylether, or diethyleneglycol dimethylether. Suitable acids for example are acetic acid, p-toluenesulfonic acid, benzensulfonic acid, hydrochloric acid or sulfuric acid. Hydrogenation with hydrogen in the presence of Raney nickel in an aprotic solvent, such as toluene or benzene, also leads to selective hydrogenation of the 3,4 double bond of the compounds of Formula II. By means of reaction with acids, the acid addition salts of the rac.-3-amino-3,4-dihydro-1-benzoxepin-5(2H)-one derivatives may be obtained from organic solvents. The separation into optical isomers (antipodes) may be effected in the above-described manner.

The 3-amino-1-benzoxepine derivatives of Formula I, which, as shown by the pharmacological tests following hereinafter, themselves exhibit valuable pharmacological effects, are also intermediate products in the preparation of the corresponding 5-hydroxy compounds of Formula I. The reduction of the keto group may be effected by means of conventional reducing agents, such as, for example, in the neutral pH range with sodium borohydride, lithium borohydride, lithium aluminum hydride, sodium-bis-(2-methoxy-ethoxy)-aluminum hydride or lithium tri-sec.-butylhydride, or in the strongly acid pH range with sodium cyanoborohydride, in the above-mentioned solvents and by using the above-mentioned acids to adjust the pH value. By selecting suitable solvents and reducing agents it is possible in the process to concentrate the racemate desired.

It is further possible to convert the compounds of Formula I, wherein $R_1$ and $R_2$, also $R_7$ and $R_8$ signify hydrogen atoms, to the N-alkyl compounds by means of subsequent alkylation. Conventional methods are employed for the reaction of these compounds with alkyl halides (see: Houben-Weyl, Vol. XI/1 (1957), p. 24ff, with dialkylsulfate, for example dimethyl- or diethyl or ethylene disulfate (see: loc. cit. p. 207), with sulfonic acid esters of the formula of $R'-SO_3R$, wherein $R'$ is for example methyl, phenyl or 4-methylphenyl and R an alkyl group (see: loc. cit. p 217) or, with ethylene and propylene oxide (see: loc. cit. p 311).

Alkylation with an aldehyde or ketone in the presence of sodium cyanoborohydride as the reducing agent, is also feasible (see: J. Org. Chem. 37, 1673, (1972).

DESCRIPTION OF THE PREFERRED EMBODIMENTS

The following examples serve to illustrate the present invention and more particularly the processes of producing the novel 3-amino-1-benzoxepine compounds of Formula I given hereinabove without, however, being limited thereto.

EXAMPLE 1

Sodium borohydride is added in small portions to a solution of 18.8 g (0.1 mole) 3-methylamino-1-benzoxepin-5-(2H)-one in a mixture of 125 ml dioxane and 125 ml acetic acid cooled in an ice bath. The reaction solution is maintained in a cooled state during the addition of the sodium borohydride (0.4 mole) up to the end of the reaction. The reaction solution is then poured into ice water, made alkaline with sodium carbonate and extracted with dichloromethane. The organic solution is washed with saturated salt solution and dried over sodium sulfate. After removal of the solvent, 16.4 g (85% of the theoretical yield) of racemic-2,3,4,5-tetrahydro-3-methylamino-1-benzoxepin-5-ol is recovered in the form of an oil.

The melting point of the hydrochloride of this compound is 152°–157° C. (isopropanol).

The separation of the isomers is undertaken from the above-mentioned oil in isopropanol by treatment with maleic acid. Through the fractionating crystallization of maleate from isopropanol and the subsequent conversion into the hydrochloride the racemic-cis-2,3,4,5-tetrahydro-3-methylamino-1-benzoxepin-5-ol hydrochloride can be obtained. The melting point of this compound is 190° C. (methanol/ether). The racemic-trans-2,3,4,5-tetrahydro-3-methylamino-1-benzoxepin-5-ol hydrochloride obtained has a melting point of 170°–173° C. (methanol/ether).

EXAMPLE 2

18.8 g (0.1 mole) 3-methylamino-1-benzoxepin-5(2H)-one is stirred with 40 g Raney Nickel in 400 ml ethanol for five hours at an hydrogen pressure of 55 bar. Subsequently, the catalyst is filtered out, the solvent is distilled off and one obtains 7.7 g (40% of the theoretical yield) racemic-2,3,4,5-tetrahydro-3-methylamino-1-benzoxepin-5-ol as an oil. The compound can be further separated as described earlier and further identified.

EXAMPLE 3

18.9 g (0.3 mole) sodium cyanoborohydride is added in small portions to a solution of 94.2 g (0.5 mole) 3-methylamino-1-benzoxepin-5(2H)-one in a mixture of 300 ml dioxane and 300 ml acetic acid. The addition is controlled such that the temperature does not reach over 25° C. Subsequently, the reaction is continued to its end point at room temperature and then the reaction solution is poured into ice water, rendered alkaline with sodium carbonate, and extracted with dichloromethane. The organic phase is washed with saturated salt solution and dried over sodium sulfate. Through introduction of hydrochloric acid the hydrochloride of the racemate 3-methylamino-3,4-dihydro-1-benzoxepin-5(2H)-one precipitates out and is subsequently removed. The yield is 89.9 g (79% of the theoretical yield) The melting point is 184°–186° C. (methanol/ether).

EXAMPLE 4

To a solution of 2.3 g (0.01 mole) 3-(n-butylamino)-1-benzoxepin-5(2H)-one in 10 ml methanol a small amount of bromocresol green is added. A solution of hydrochloric acid in methanol (approximately 3 n) is added dropwise until the change in indicator. Subsequently, a solution of 0.65 g sodium cyanoborohydride (0.01 mole) in 10 ml methanol is slowly added at room temperature and stirred for one to two hours until the end of the reaction. Thereby the solution is subjected to a dropwise addition of hydrochloric acid in methanol to maintain the yellow indicator color. The solvent is distilled off followed by recovery of the product in water, rendered alkaline with the addition of dimethylamine and extracted with ether. The etheral solutions are combined and dried with sodium sulfate. Through the introduction of hydrochloric acid the racemic 3-n-butylamino-3,4-dihydro-1-benzoxepin-5(2H)-one hydrochloride is precipitated out. The product is redissolved and recrystallized. The yield is 2.0 g (74.1% of the theoretical yield) with a melting point of 154°–158° C. (isopropanol/ether).

EXAMPLE 5

27.9 g (0.1 mole) 3-phenylethylamino-1-benzoxepin-5(2H)-one are stirred with 25 g Raney Nickel in 350 ml toluene for 20 hours at a hydrogen pressure of 150 bar. Subsequently, the catalyst is filtered away and the solvent is distilled off followed by recovery of the product in methanol. After introduction of hydrochloric acid 14.6 g(46% of the theoretical yield) racemic 3-phenylethylamino-3,4-dihydro-1-benzoxepin-5(2H)-one hydrochloride is obtained. The product gives a melting point of 160° C. in methanol (decomposing).

EXAMPLE 6

According to the procedure of Examples 3 through 5, the following:

3-methylamino-7-methyl-1-benzoxepin-5(2H)-one
3-methylamino-7-ethyl-1-benzoxepin-5(2H)-one
3-methylamino-7-bromo-1-benzoxepin-5(2H)-one
3-methylamino-7-methoxy-1-benzoxepin-5(2H)-one
3-methylamino-8-methoxy-1-benzoxepin-5(2H)-one
3-pyrrolidino-1-benzoxepin-5(2H)-one
3-methylamino-7,8-dichloro-1-benzoxepin-5(2H)-one
3-methylamino-7,8-dimethyl-1-benzoxepin-5(2H)-one
3-isopropylamino-1-benzoxepin-5(2H)-one
3-benzylamino-1-benzoxepin-5(2H)-one
3-dimethylamino-1-benzoxepin-5(2H)-one
3-piperidino-1-benzoxepin-5(2H)-one
3-morpholino-1-benzoxepin-5(2H)-one
3-(γ-dimethylamino-propylamino)-7-chloro-1-benzoxepin-5(2H)-one
3-(γ-dimethylamino-propylamino)-1-benzoxepin-5(2H)-one
3-(β-dimethylamino-ethylamino)-1-benzoxepin-5(2H)-one
3-ammino-1-benzoxepin-5(2H)-one
3-(β-methoxy-ethylamino)-1-benzoxepin-5(2H)-one
can be converted into the following compounds

| | Melting Point C.° |
|---|---|
| rac.-3-methylamino-3,4-dihydro-7-methyl-1-benzoxepin-5(2H)-one hydrochloride | 183–185* |
| rac.-3-methylamino-3,4-dihydro-7-ethyl-1-benzoxepin-5(2H)-one hydrochloride | 146–148 |
| rac.-3-methylamino-3,4-dihydro-7-bromo-1-benzoxepin-5(2H)-one hydrochloride | 193–195* |
| rac.-3-methylamino-3,4-dihydro-7-methoxy-1-benzoxepin-5(2H)-one hydrochloride | 178–180* |
| rac.-3-methylamino-3,4-dihydro-8-methoxy-1-benzoxepin-5(2H)-one hydrochloride | 168–170 |
| rac.-3-pyrrolidino-3,4-dihydro-1-benzoxepin-5(2H)-one hydrochloride | 128–130 |
| rac.-3-methylamino-3,4-dihydro-7,8-dichloro-1-benzoxepin-5(2H)-one hydrochloride | 194* |
| rac.-3-methylamino-3,4-dihydro-7,8-dimethyl-1-benzoxepin-5(2H)-one hydrochloride | 206* |
| rac.-3-isopropylamino-3,4-dihydro-1-benzoxepin-5(2H)-one hydrochloride | 171–175 |
| rac.-3-benzylamino-3,4-dihydro-1-benzoxepin-5(2H)-one hydrochloride | 141–145 |
| rac.-3-dimethylamino-3,4-dihydro-1-benzoxepin-5(2H)-one maleate | 107–109 |
| rac.-3-piperidino-3,4-dihydro-1-benzoxepin-5(2H)-one hydrochloride | 154–156 |
| rac.-3-morpholino-3,4-dihydro-1-benzoxepin-5(2H)-one hydrochloride | 148–150 |
| rac.-3-(γ-dimethylamino-propylamino)-3,4-dihydro-7-chloro-1-benzoxepin-5(2H)-one dihydrochloride monohydrate | 150–154 |
| rac.-3-(γ-dimethylamino-propylamino)-3,4-dihydro-1-benzoxepin-5(2H)-one dihydrochloride | 154–158 |
| rac.-3-(β-dimethylamino-ethylamino)-3,4-dihydro-1-benzoxepin-5(2H)-one dihydrochloride | 150–157 |
| rac.-3-amino-3,4-dihydro-1-benzoxepin-5(2H)-one hydrochloride | 211* |
| rac.-3-(β-methoxy-ethylamino)-3,4-dihydro-1-benzoxepin-5(2H)-one hydrochloride | 133–135 |

*Decomposing

EXAMPLE 7

To a cooled solution of 33.5 g (0.1 mole) racemic-3-(γ-dimethylamino-propylamino)-3,4-dihydro-1-benzoxepin-5(2H)-one dihydrochloride in 300 ml methanol is added sodium borohydride in small portions up to the end of the reaction. The reaction solution is acidified with hydrochloric acid and evaporated to dryness. The residue is washed with water and rendered alkaline with aqueous ammonium solution and subsequently extracted with dichloromethane. After the washing of the organic phase with suitable salt solution, drying over sodium sulfate, and evaporation 23.8 g (90% of the theoretical yield) of racemic-2,3,4,5-tetrahydro-3-(γ-dimethylamino-propylamino)-1-benzoxepin-5-ol is recovered as an oily residue. Through chromotography on a silica gel on subsequent formation of the dimaleate rac.-cis-2,3,4,5-tetrahydro-3-(γ-dimethylamino-propylamino)-1-benzoxepin-5-ol dimaleate is obtained with a melting point of 169°–170° C. (methanol). rac.-trans-2,3,4,5-tetrahydro-3-(γ-dimethylamino-propylamino)-1-benzoxepin-5-ol dimaleate is also recovered with a melting point of 157°–159° C. (methanol).

EXAMPLE 8

To a boiling solution of 80 g (0.5 mole) rac.-3-methylamino-3,4-dihydro-1-benzoxepin-5-(2H)-one in a mixture of 550 ml toluene and 300 ml hexane, 550 ml of a 1 molar solution of lithium-tri-sec.-butylborohydride in tetrahydrofuran are added in drops, so that the solution is maintained boiling. Following the completion of the addition, the mixture is heated to boiling for another hour. After cooling, the mixture is acidified by the drop-wise addition of methanolic hydrochloric acid. The methanol phase is then separated and the toluene/hexane mixture is again extracted with hydrochloric acid in methanol. The extracts are evaporated, taken up with dichloromethane and a solution (10%) of sodium carbonate, the organic phase washed with saturated sodium chloride, dried over sodium sulfate and evaporated to dryness. 67.6 g (70% of the theoretical yield) of rac.-2,3,4,5-tetrahydro-3-methylamino-1-benzoxepin-5-ol are obtained in the form of an oily residue, wherein rac.-cis-2,3,4,5-tetrahydro-3-methylamino-1-benzoxepin-5-ol predominates with 82 parts for 18 parts of rac.-trans-2,3,4,5-tetrahydro-3-methylamino-1-benzoxepin-5-ol. The compounds may be separated and identified as described hereinabove.

EXAMPLE 9

To a solution of 3.9 g (0.02 mole) rac.-trans-2,3,4,5-tetrahydro-3-methylamino-1-benzoxepin-5-ol, 80 ml of acetonitrile and 17.1 ml of aqueous formaldehyde solution (35%) are added 3.9 g (0.06 mole) sodium cyanoborohydride. Subsequently, 2.1 ml glacial acetic acid is added and the mixture is stirred at room temperature for two hours. The solution is diluted with 270 ml ether and washed with a diluted solution of caustic soda. It is then dried over sodium sulfate and evaporated. The residue is dissolved with methanol and rac.-trans-2,3,4,5-tetrahydro-3-dimethylamino-1-benzoxepin-5-ol is isolated as the maleate. The yield is 3.9 g (60% of the theoretical yield) with a melting point of 157°–158° C. (methanol/ether).

EXAMPLE 10

According to the procedures of the foregoing examples and by known techniques the following 3-amino-1-benzoxepines, namely
3-amino-1-benzoxepin-5(2H)-one
3-(n-butylamino)-1-benzoxepin-5(2H)-one
3-benzylamino-1-benzoxepin-5(2H)-one
3-phenathylamino-1-benzoxepin-5(2H)-one
3-dimethylamino-1-benzoxepin-5(2H)-one
3-diethylamino-1-benzoxepin-5(2H)-one
3-pyrrolidino-1-benzoxepin-5(2H)-one
3-piperidino-1-benzoxepin-5(2H)-one
3-morpholino-1-benzoxepin-5(2H)-one
3-methylamino-7-ethyl-1-benzoxepin-5(2H)-one
3-methylamino-7-chloro-1-benzoxepin-5(2H)-one
3-methylamino-8-chloro-1-benzoxepin-5(2H)-one
3-methylamino-7-bromo-1-benzoxepin-5(2H)-one
3-methylamino-7-methoxy-1-benzoxepin-5(2H)-one
3-methylamino-7-chloro-8-methyl-1-benzoxepin-5(2H)-one
3-(γ-dimethylamino-propylamino)-7-chloro-1-benzoxepin-5(2H)-one
3-(β,β-dimethyl-γ-dimethylamino-propylamino)-1-benzoxepin-5(2H)-one
3-(β-methoxy-ethylamino)-1-benzoxepin-5(2H)-one
3-methylamino-7-methyl-1-benzoxepin-5(2H)-one
3-methylamino-8-methoxy-1-benzoxepin-5(2H)-one
3-methylamino-7,8-dichloro-1-benzoxepin-5(2H)-one
3-methylamino-7,8-dimethyl-1-benzoxepin-5(2H)-one
are used to produce the following compounds

| | Melting Point C.° |
|---|---|
| rac.-cis-2,3,4,5-tetrahydro-3-amino-1-benzoxepin-5-ol hydrochloride | 222* |
| rac.-trans-2,3,4,5-tetrahydro-3-amino-1-benzoxepin-5-ol hydrochloride | 160–162 |
| rac.-cis-2,3,4,5-tetrahydro-3-(n-butylamino)-1-benzoxepin-5-ol toluene-4-sulfonate | 148–150 |
| rac.-trans-2,3,4,5-tetrahydro-3-(n-butylamino)-1-benzoxepin-5-ol toluene-4-sulfonate | 187–189 |
| rac.-cis-2,3,4,5-tetrahydro-3-benzylamino-1-benzoxepin-5-ol maleate | 176–178 |
| rac.-trans-2,3,4,5-tetrahydro-3-benzylamino-1-benzoxepin-5-ol maleate | 133–135 |
| rac.-cis-2,3,4,5-tetrahydro-3-phenethylamino-1-benzoxepin-5-ol maleate | 162–164 |
| rac.-trans-2,3,4,5-tetrahydro-3-phenethylamino-1-benzoxepin-5-ol maleate | 182–184 |
| rac.-cis-2,3,4,5-tetrahydro-3-dimethylamino-1-benzoxepin-5-ol maleate | 176–179 |
| rac.-trans-2,3,4,5-tetrahydro-3-dimethylamino-1-benzoxepin-5-ol maleate | 157–158 |
| rac.-cis-2,3,4,5-tetrahydro-3-diethylamino-1-benzoxepin-5-ol toluene-4-sulfonate | 185–187 |
| rac.trans-2,3,4,5-tetrahydro-3-diethylamino-1-benzoxepin-5-ol toluene-4-sulfonate | 130–131 |
| rac.-cis-2,3,4,5-tetrahydro-3-pyrrolidino-1-benzoxepin-5-ol toluene-4-sulfonate | 163–165 |
| rac.-trans-2,3,4,5-tetrahydro-3-pyrrolidino-1-benzoxepin-5-ol toluene-4-sulfonate | 158–160 |
| rac.-cis-2,3,4,5-tetrahydro-3-piperidino-1-benzoxepin-5-ol toluene-4-sulfonate | 178–179 |
| rac.-trans-2,3,4,5-tetrahydro-3-piperidino-1-benzoxepin-5-ol toluene-4-sulfonate | 142–144 |
| rac.-cis-2,3,4,5-tetrahydro-3-morpholino-1-benzoxepin-5-ol toluene-4-sulfonate | 154–156 |
| rac.-trans-2,3,4,5-tetrahydro-3-morpholino-1-benzoxepin-5-ol toluene-4-sulfonate | 145–146 |
| rac.-cis-2,3,4,5-tetrahydro-3-methylamino-7-ethyl-1-benzoxepin-5-ol hydrochloride | 138–140 |
| rac.-trans-2,3,4,5-tetrahydro-3-methylamino-7-ethyl-1-benzoxepin-5-ol hydrochloride | 197–198 |
| rac.-cis-2,3,4,5-tetrahydro-3-methylamino-7-chloro-1-benzoxepin-5-ol hydrochloride | 172–173 |
| rac.-trans-2,3,4,5-tetrahydro-3-methylamino-7-chloro-1-benzoxepin-5-ol hydrochloride | 242* |
| rac.-cis-2,3,4,5-tetrahydro-3-methylamino-8-chloro-1-benzoxepin-5-ol hydrochloride | 194–195 |
| rac.-trans-2,3,4,5-tetrahydro-3-methylamino-8-chloro-1-benzoxepin-5-ol hydrochloride | 189–190 |
| rac.-cis-2,3,4,5-tetrahydro-3-methylamino-7-bromo-1-benzoxepin-5-ol hydrochloride | 186–188 |
| rac.-trans-2,3,4,5-tetrahydro-3-methylamino-7-bromo-1-benzoxepin-5-ol hydrochloride | 243* |
| rac.-cis-2,3,4,5-tetrahydro-3-methylamino-7-methoxy-1-benzoxepin-5-ol hydrochloride | 198–200 |
| rac.-trans-2,3,4,5-tetrahydro-3-methylamino-7-methoxy-1-benzoxepin-5-ol hydrochloride | 223–225 |

| -continued | Melting Point C.° |
|---|---|
| rac.-cis-2,3,4,5-tetrahydro-3-methylamino-7-chloro-8-methyl-1-benzoxepin-5-ol hydrochloride | 233* |
| rac.-trans-2,3,4,5-tetrahydro-3-methylamino-7-chloro-8-methyl-1-benzoxepin-5-ol hydrochloride | 243* |
| rac.-cis-2,3,4,5-tetrahydro-3-(γ-dimethylamino propylamino)-7-chloro-1-benzoxepin-5-ol dihydrochloride | 168–170 |
| rac.-cis-2,3,4,5-tetrahydro-3-(β,β-dimethyl-γ-dimethylamino-propylamino)-benzoxepin-5-ol dimaleate | 151–153 |
| rac.-trans-2,3,4,5-tetrahydro-3-(β,β-dimethyl-γ-dimethylamino-propylamino)-1-benzoxepin-5-ol dimaleate | 122–124 |
| rac.-cis-2,3,4,5-tetrahydro-3-(β-methoxyethylamino)-1-benzoxepin-5-ol cyclohexylaminosulfonate | 162–164 |
| rac.-trans-2,3,4,5-tetrahydro-3-(β-methoxyethylamino)-1-benzoxepin-5-ol cyclohexylaminosulfonate | 132–133 |
| rac.-cis-2,3,4,5-tetrahydro-3-methylamino-7-methyl-1-benzoxepin-5-ol hydrochloride | 199–200 |
| rac.-trans-2,3,4,5-tetrahydro-3-methylamino-7-methyl-1-benzoxepin-5-ol hydrochloride | 204–205 |
| rac.-cis-2,3,4,5-tetrahydro-3-methylamino-8-methoxy-1-benzoxepin-5-ol hydrochloride | 152–153 |
| rac.-trans-2,3,4,5-tetrahydro-3-methylamino-8-methoxy-1-benzoxepin-5-ol hydrochloride | 139–141 |
| rac.-cis-2,3,4,5-tetrahydro-3-methylamino-7,8-dichloro-1-benzoxepin-5-ol hydrochloride | 245* |
| rac.-trans-2,3,4,5-tetrahydro-3-methylamino-7,8-dichloro-1-benzoxepin-5-ol hydrochloride | 246* |
| rac.-cis-2,3,4,5-tetrahydro-3-methylamino-7,8-dimethyl-1-benzoxepin-5-ol hydrochloride | 198* |
| rac.-trans-2,3,4,5-tetrahydro-3-methylamino-7,8-dimethyl-1-benzoxepin-5-ol hydrochloride | 208* |

*Decomposing

UTILITY AND TESTS

As stated hereinabove, it is an important feature of the present invention to provide the medical profession with novel and highly effective therapeutic agents for restoring the physiological motility and unimpeded passage of food through the stomach.

Surprisingly, it was found that the 3-amino-1-benzoxepine compounds of Formula I, according to the present invention, have such an effect. The peristaltic wave-like movements of the stomach are intensified under their action as can be shown in animal experiments. Due thereto the frequency of the movements decreases in favor of more vigorous, more deeply constricting and contracting wave-like movements. The effects demonstrated in these animal experiments allow us to assume that a considerable improvement of the discharging ability of the stomach is achieved.

DESCRIPTION OF THE PHARMACOLOGICAL TEST METHODS

1. Determination of the Acute Toxicity.

The acute seven-day toxicity is determined by intraperitoneal administration of a single dose of the respective compound to a fasting white NMRI mouse. The $LD_{50}$-values are calculated via electronic data processing by a probit analysis as described in the book "Grundbegriffe der Biometrie" (Basic Biometrical Definitions) by L. Cavalli-Sforza, page 153 et seq., published by Gustav Fischer Verlag, Stuttgart, 1964.

2. Testing of the Gastric Peristalsis.

To determine the functioning of the gastric peristalsis, rats weighing about 200 g are narcotized by means of ketamine hydrochloride and xylazine. A catheter is introduced into the Vena jugularis of the narcotized rats and a tracheal catheter into the trachea. A stomach probe is inserted into their stomach and tied thereto. The probe is connected via a three-way cock with a Statham pressure imparting device (P 23 DB). The stomach is sealed off by a ligature at the pylorus and at the cardia. The stomach is filled with 3 ml of an 0.9% aqueous sodium chloride solution. The pressure waves produced by the stomach are continuously registered by a suitable recording device such as by a Watanabe Multicorder (MC 641). In order to determine the effect of the compounds to be tested, they are dissolved in physiological sodium chloride solution or are suspended in Tylose MH 50 solution. Said solutions or suspensions are administered intraperitoneally to the rats in a dose of 20 mg/kg. The amplitudes and frequencies of the pressure wave-like movements of the stomach as they occur before and after administration of the compound to be tested, are compared.

Evaluation of the test results show that a considerable increase in the amplitudes takes place shortly after administration of the compounds according to the present invention. This effect in combination with a pronounced decrease in the frequencies of varying magnitude results in an improved food passage through the stomach.

The following 3-amino-1-benzoxepine compounds were tested according to these methods:

(A) rac.-cis-2,3,4,5-tetrahydro-3-methylamino-1-benzoxepin-5-ol
(A') rac.-trans-2,3,4,5-tetrahydro-3-methylamino-1-benzoxepin-5-ol
(B) rac.-cis-2,3,4,5-tetrahydro-3-methylamino-8-chloro-1-benzoxepin-5-ol
(B') rac.-trans-2,3,4,5-tetrahydro-3-methylamino-8-chloro-1-benzoxepin-5-ol
(C) rac.-cis-2,3,4,5-tetrahydro-3-isopropylamino-1-benzoxepin-5-ol
(C') rac.-trans-2,3,4,5-tetrahydro-3-isopropylamino-1-benzoxepin-5-ol
(D) rac.-cis-2,3,4,5-tetrahydro-3-benzylamino-1-benzoxepin-5-ol
(D') rac.-trans-2,3,4,5-tetrahydro-3-benzylamino-1-benzoxepin-5-ol
(E) rac.-cis-2,3,4,5-tetrahydro-3-(γ-dimethylaminopropylamino)-1-benzoxepin-5-ol
(E') rac.-trans-2,3,4,5-tetrahydro-3-(γ-dimethylaminopropylamino)-1-benzoxepin-5-ol
(F) rac.-cis-2,3,4,5-tetrahydro-3-diethylamino-1-benzoxepin-5-ol
(F') rac.-trans-2,3,4,5-tetrahydro-3-diethylamino-1-benzoxepin-5-ol
(G) rac.-cis-2,3,4,5-tetrahydro-3-methylamino-7-chloro-1-benzoxepin-5-ol
(G') rac.-trans-2,3,4,5-tetrahydro-3-methylamino-7-chloro-1-benzoxepin-5-ol
(H) rac.-cis-2,3,4,5-tetrahydro-3-(n-butylamino)-1-benzoxepin-5-ol
(H') rac.-trans-2,3,4,5-tetrahydro-3-(n-butylamino)-1-benzoxepin-5-ol
(I) rac.-cis-2,3,4,5-tetrahydro-3-morpholino-1-benzoxepin-5-ol
(I') rac.-trans-2,3,4,5-tetrahydro-3-morpholino-1-benzoxepin-5-ol
(K) rac.-cis-2,3,4,5-tetrahydro-3-pyrrolidino-1-benzoxepin-5-ol (K') rac.-trans-2,3,4,5-tetrahydro-3-pyrrolidino-1-benzoxepin-5-ol
(L) rac.-cis-2,3,4,5-tetrahydro-3-phenethylamino-1-benzoxepin-5-ol
(L') rac.-trans-2,3,4,5-tetrahydro-3-phenethylamino-1-benzoxepin-5-ol
(M) rac.-cis-2,3,4,5-tetrahydro-3-methylamino-7,8-dichloro-1-benzoxepin-5-ol
(M') rac.-trans-2,3,4,5-tetrahydro-3-methylamino-7,8-dichloro-1-benzoxepin-5-ol
(N) rac.-cis-2,3,4,5-tetrahydro-3-amino-1-benzoxepin-5-ol
(N') rac.-trans-2,3,4,5-tetrahydro-3-amino-1-benzoxepin-5-ol
(O) rac.-cis-2,3,4,5-tetrahydro-3-dimethylamino-1-benzoxepin-5-ol
(O') rac.-trans-2,3,4,5-tetrahydro-3-dimethylamino-1-benzoxepin-5-ol
(1) rac.-3-methylamino-3,4-dihydro-1-benzoxepin-5(2H)-one
(2) rac.-3-isopropylamino-3,4-dihydro-1-benzoxepin-5(2H)-one
(3) rac.-3-benzylamino-3,4-dihydro-1-benzoxepin-5(2H)-one
(4) rac.-3-($\gamma$-dimethylamino-propylamino)-3,4-dihydro-1-benzoxepin-5(2H)-one
(5) rac.-3-dimethylamino-3,4-dihydro-1-benzoxepin-5(2H)-one
(6) rac.-3-($\gamma$-dimethylamino-propylamino)-7-chloro-3,4-dihydro-1-benzoxepin-5(2H)-one
(7) rac.-3-(n-butylamino)-3,4-dihydro-1-benzoxepin-5(2H)-one.

The following table shows the results obtained on determination amplitudes and frequencies of gastric peristalsis determined as described hereinabove.

TABLE
MEASUREMENT OF THE GASTRIC PRESSURE

| Compound Tested | Factor of the Increase in Amplitude | Frequency Decrease in % | $LD_{50}$ i.p. (mg/kg) |
|---|---|---|---|
| A | 5.6 | 3.0 | 342 |
| A' | 8.8 | 12.7 | 285 |
| B | 9.6 | 31.0 | 200 |
| B' | 4.5 | 4.0 | 83 |
| C | 6.3 | 13.0 | 272 |
| C' | 12.5 | 23.0 | 664 |
| D | 7.6 | 21.0 | 92 |
| D' | 12.4 | 31.0 | 113 |
| E | 22.9 | 32.0 | 664 |
| E' | 25.6 | 18.0 | 590 |
| F | 9.5 | 13.0 | 183 |
| F' | 8.9 | 28.0 | 219 |
| G | 13.5 | 10.0 | n.b. |
| G' | 11.0 | 26.0 | n.b. |
| H | 32.3 | 36.0 | n.b. |
| H' | 15.3 | 8.0 | n.b. |
| I | 0 | 0 | n.b. |
| I' | 2.2 | 12.0 | n.b. |
| K | 9.7 | 10.0 | n.b. |
| K' | 18.3 | 20.0 | n.b. |
| L | 12.6 | 21.0 | n.b. |
| L' | 15.9 | 10.0 | n.b. |
| M | 6.9 | 22.0 | n.b. |
| M' | 6.0 | 9.0 | n.b. |
| N | 8.1 | 0 | n.b. |
| N' | 12.0 | 30.0 | n.b. |
| O | 5.8 | 7.0 | n.b. |
| O' | 17.2 | 8.0 | n.b. |
| 1 | 1.6 | 8.0 | 137 |
| 2 | 2.6 | 16.0 | 183 |
| 3 | 3.6 | 7.0 | 253 |
| 4 | 3.7 | 25.0 | 272 |
| 5 | 1.3 | 12.0 | 285 |
| 6 | 3.4 | 29.0 | 296 |
| 7 | 6.6 | 28.0 | n.b. |

*n.b. indicates test results are not known

The preceding Table contains the measured values. The results given in the Table clearly show that even small doses of the compounds according to the present invention and their acid addition salts cause a significant intensification of the peristaltic wavelike movements of the stomach. At the same time, the high activity and the low toxicity of the tested compounds indicate that they are well compatible. A further advantage of the compounds tested is the observed rapid onset of their physiological action.

The pharmacologically observed effects clearly indicate that the compounds according to the present invention are capable of overcoming or at least alleviating disorders and disturbances of the gastro-intestinal functions of the human body, such as, for instance, stenoses of the pylorus, duodeno-gastric reflux as well as atonic conditions. A favorable therapeutic effect can furthermore be expected in functional disorders which cause pain in the upper abdominal region of the body, nausea, a sense of fullness, and other unpleasant symptoms, such as the disagreeable symptoms encountered in the case of an ulcus ventriculi and ulcus duodeni, gastritis and nervous irritation of the stomach. Furthermore, an increased passage of an X-ray contrast agent through the stomach is achieved by administration of the compounds according to the present invention. This effect is highly desirable in the X-ray diagnosis of the gastro-intestinal tract.

Suitable pharmaceutical preparations according to the present invention contain, as effective agents, the 3-amino-1-benzoxepine compounds of Formula I or their pharmacologically compatible acid addition salts in combination with conventional pharmaceutically acceptable excipients, such as carrier materials and/or diluents. The resulting pharmaceutical preparations can be administered orally or parenterally. Suitable preparations are in the form of tablets, capsules, lozenges, sirups, dry powders, injectable or infusible solutions or suspensions. They can also be prepared and administered in the form of suppositories. The preferred preparations are those which can be orally administered.

The dosage to be administered of the pharmaceutical compounds according to the present invention is dependent on various factors, such as the kind and the seriousness of the disease or the compound to be administered. In general, a single dose of between 0.1 mg and 20 mg and preferably between 0.5 mg to 10 mg, administered orally, is sufficient to achieve satisfactory results.

The following example illustrates the preparation of an orally administrable composition without, however, being limited thereto.

EXAMPLE 11

Capsules containing rac.-cis-2,3,4,5-tetrahydro-3-methylamino-1-benzoxepin-5-ol as the active compound.

Each capsule contains an intimate mixture of the following ingredients:

| | |
|---|---|
| Pharmacologically Active Compound | 10 mg |
| Lactose | 65 mg |
| Dried Corn Starch | 40 mg |
| Soluble Starch | 4 mg |
| Magnesium stearate | 1 mg |
| Total Content of Each Capsule | 120 mg |

Production Method

The pharmacologically active compound is mixed with the lactose and dried corn starch. The resultant mixture is thoroughly wetted with a 15% aqueous solution of the soluble starch and granulated. The damp mass is passed through a 1.6 mm sieve, dried at 40° C. and finally passed through a 1.0 mm sieve. The resulting mixture is encapsuled in amounts of 120 mg after the mixing of the granulates with magnesium stearate. In this fashion each capsule contains 10 mg of the pharmacologically active compound.

Of course, many changes and variations in the process of producing the compounds of Formula I according to the present invention and of their acid addition salts, in the reactants and solvents used, in the reaction conditions, temperature, pressure and duration, in the manner of working up the reaction mixture and of isolating and purifying the resulting reaction products, in the preparation of pharmaceutical compositions containing said 3-amino-1-benzoxepine compounds and their acid addition salts, in the method of administering said pharmaceutical compositions for the treatment of motility disorders of the gastrointestinal tract, and the like may be made by those skilled in the art in accordance with the principles set forth herein and in the claims annexed hereto.

What is claimed is:

1. 3-amino-1-benzoxepine derivatives of the following Formula I:

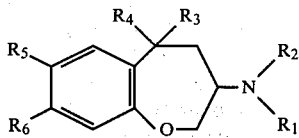

wherein:
R$_1$ and R$_2$ independently of one another are
hydrogen,
C$_1$–C$_5$ alkyl,
C$_1$–C$_5$ alkyl substituted with a terminal phenyl, or a phenyl containing one or two halogens, methyl or methoxy groups, a 3,4-methylenedioxy or a 3,4-ethylenedioxy group,
C$_2$–C$_5$ alkyl substituted with terminal hydroxy or methoxy or,
C$_3$–C$_4$ alkenyl; or
one of R$_1$ and R$_2$ are hydrogen or a C$_1$–C$_5$ alkyl and the other is a C$_2$–C$_5$ alkyl substituted with a terminal NR$_7$R$_8$;

R$_7$ and R$_8$ independently of one another are hydrogen or C$_1$–C$_5$ alkyl; or
R$_7$ and R$_8$ are together a 5 to 7 member ring or said ring having heterogeneous oxygen, sulfur or nitrogen, or
R$_1$ and R$_2$ are together a 5 to 7 member ring or said ring having heterogeneous oxygen, sulfur or NR$_9$;
R$_9$ is hydrogen, methyl, benzyl, or phenyl;
one of R$_3$ and R$_4$ is hydrogen and the other hydroxy, or R$_3$ and R$_4$ together are oxygen;
R$_5$ and R$_6$ independently of one another are hydrogen, halogen, C$_1$–C$_4$ alkyl, C$_1$–C$_4$ alkoxy or C$_1$–C$_4$ alkylthio; or
one of R$_5$ and R$_6$ is trifluoromethyl or nitro and the other is hydrogen; the stereo isomers and the acid addition salts thereof.

2. The 3-amino-1-benzoxepine derivative of claim 1 comprising the cis- and trans-racemates of 2,3,4,5-tetrahydro-3-A-1-benzoxepin-5-ol wherein A is selected from the group consisting of amino, methylamino, dimethylamino, diethylamino, β-methoxyethylamino, isopropylamino, n-butylamino, benzylamino, phenethylamino, morpholino, pyrrolidino, piperidino, γ-dimethylamino-propylamino and β,β-dimethyl-γ-dimethylamino-propylamino.

3. The 3-amino-1-benzoxepine derivative of claim 1 comprising the cis- and trans-racemates of 2,3,4,5-tetrahydro-3-methylamino-7B,8C-1-benzoxepin-5-ol wherein B is selected from the group consisting of hydrogen, chloro, bromo, methyl, ethyl and methoxy and C is selected from the group consisting of hydrogen, chloro, methyl and methoxy.

4. The 3-amino-1-benzoxepine derivative of claim 1 comprising rac.-cis-2,3,4,5-tetrahydro-3-(γ-dimethylaminopropylamino)-7-chloro-1-benzoxepin-5-ol.

5. The 3-amino-1-benzoxepine derivative of claim 1 comprising rac.-3-A-3,4-dihydro-1-benzoxepin-5(2H)-one wherein A is selected from the group consisting of amino, methylamino, dimethylamino, isopropylamino, n-butylamino, benzylamino, phenethylamino, morpholino, pyrrolidino, piperidino, β-methoxy-ethylamino, β-dimethylamino-ethylamino, and γ-dimethylamino-propylamino.

6. The 3-amino-1-benzoxepine derivative of claim 1 comprising rac.-3-methylamino-3,4-dihydro-7B,8C-1-benzoxepin-5(2H)-one wherein B is selected from the group consisting of hydrogen, chloro, bromo, methyl, ethyl and methoxy and C is selected from the group consisting of hydrogen, chloro, methyl and methoxy.

7. The 3-amino-1-benzoxepine derivative of claim 1 comprising rac.(γ-dimethylamino-propylamino)-3,4-dihydro-7-chloro-1-benzoxepin-5(2H)-one.

8. A pharmaceutical composition comprising an effective amount of the 3-amino-1-benzoxepine derivative of claim 1 and a pharmaceutically acceptable excipient.

9. A method of treating motility disorders of the gastrointestinal tract comprising administering an effective amount of 3-amino-1-benzoxepine derivative of claim 1.

* * * * *